United States Patent
Park et al.

(10) Patent No.: US 11,861,454 B2
(45) Date of Patent: Jan. 2, 2024

(54) METHOD FOR DETECTING ANOMALY IN TIME SERIES DATA AND COMPUTING DEVICE FOR EXECUTING THE METHOD

(71) Applicant: University-Industry Cooperation Group of Kyung Hee University, Gyeonggi-do (KR)

(72) Inventors: Gyeong Moon Park, Gyeonggi-do (KR); A Hyung Shin, Gyeonggi-do (KR)

(73) Assignee: University-Industry Cooperation Group of Kyung Hee University, Gyeonggi-do (KR)

( * ) Notice: Subject to any disclaimer, the term of this patent is extended or adjusted under 35 U.S.C. 154(b) by 0 days.

(21) Appl. No.: 17/878,181

(22) Filed: Aug. 1, 2022

(65) Prior Publication Data

US 2023/0179496 A1  Jun. 8, 2023

(30) Foreign Application Priority Data

Dec. 8, 2021 (KR) .......................... 10-2021-0175107

(51) Int. Cl.
*G06N 3/0895* (2023.01)
*H04L 43/067* (2022.01)
*H04L 43/0817* (2022.01)
*G06F 18/214* (2023.01)
*G01W 1/10* (2006.01)
*A61B 5/024* (2006.01)

(52) U.S. Cl.
CPC ....... *G06N 3/0895* (2023.01); *A61B 5/02422* (2013.01); *G01W 1/10* (2013.01); *G06F 18/214* (2023.01); *H04L 43/067* (2013.01); *H04L 43/0817* (2013.01)

(58) Field of Classification Search
CPC .......... G06N 3/0895; G06N 3/08; G06N 3/04; G06N 3/0455; A61B 5/02422; A61B 5/725; A61B 5/7217; A61B 5/7278; G01W 1/10
See application file for complete search history.

(56) References Cited

U.S. PATENT DOCUMENTS

| 2016/0029968 A1* | 2/2016 | Lerner ............... A61B 5/02422 600/595 |
| 2022/0366237 A1* | 11/2022 | Cai ...................... G06N 3/0895 |
| 2023/0168411 A1* | 6/2023 | Marvaniya .............. G01W 1/10 706/12 |

FOREIGN PATENT DOCUMENTS

KR  10-2019-0017121 A   2/2019

* cited by examiner

*Primary Examiner* — Kyung H Shin
(74) *Attorney, Agent, or Firm* — The PL Law Group, PLLC

(57) ABSTRACT

A method of detecting an abnormality in time series data according to an embodiment of the present disclosure is performed in a computing device including one or more processors and a memory storing one or more programs executed by the one or more processors. First masking is performed to cover a portion of input time series data with a mask. First-restored time series data in which the time series data is restored is generated by inputting the first-masked time series data to a generator. A difference between the first-restored time series data and original time series data is calculated. Second masking is performed to cover a portion of the time series data with a mask on basis of the calculated difference. Second-restored time series data in which the time series data is restored is generated by inputting the second-masked time series data to the generator.

23 Claims, 8 Drawing Sheets

METHOD FOR DETECTING ANOMALY IN TIME SERIES DATA AND COMPUTING DEVICE FOR EXECUTING THE METHOD

CROSS REFERENCE TO RELATED APPLICATION AND CLAIM OF PRIORITY

This application claims the benefit under 35 USC § 119 of Korean Patent Application No. 10-2021-0175107, filed on Dec. 8, 2021, in the Korean Intellectual Property Office, the entire disclosure of which is incorporated herein by reference for all purposes.

BACKGROUND

1. Field

Embodiments of the present disclosure relate to a technology for detecting an abnormality in time series data.

2. Description of the Related Art

As the Internet of things (IoT), sensors, and the like are used in a variety of fields, various types of time series data (e.g., heart rate, brain waves, temperature, and moisture) may be obtained therefrom. When such time series data significantly deviates from a specific pattern, such a deviation is detected as an abnormality.

Recently, technology for learning a variety of patterns within time series data using deep learning technology and for detecting an abnormality on the basis of the learned time series data has been developed. A conventional deep learning model for detecting an abnormality in time series data uses an autoencoder based on a convolutional neural network (CNN) or an autoencoder based on a recurrent neural network (RNN).

However, such a CNN-based deep learning model (e.g., BeatGAN) is a model specialized for processing data embodied in the form of a lattice, rather than processing time series data with time order. Such an RNN-based deep learning model (e.g., RAMED) uses multi-resolution decoders to capture time features of data with a variety of resolutions. This model has the problem of increasing the size of the neural network.

The information disclosed in the Background section is only provided for a better understanding of the background and should not be taken as an acknowledgment or any form of suggestion that this information forms prior art that would already be known to a person having ordinary skill in the art.

SUMMARY

Various aspects of the present disclosure provide a method of detecting an abnormality in time series data and a computing device for executing the same method, the method and device being able to reduce the volume of a neural network and improve abnormality detection performance.

According to an embodiment, provided is a method of detecting an abnormality in time series data, the method being performed in a computing device including one or more processors and a memory storing one or more programs executed by the one or more processors. The method may include: first masking to cover a portion of input time series data with a mask; generating first-restored time series data in which the time series data is restored by inputting the first-masked time series data to a generator; calculating a difference between the first-restored time series data and original time series data; second masking to cover a portion of the time series data with a mask on basis of the calculated difference; and generating second-restored time series data in which the time series data is restored by inputting the second-masked time series data to the generator.

The first masking may randomly cover the portion of the input time series data. The second masking may cover the portion of the time series data, in which the difference between the first-restored time series data and the original time series data is equal to or greater than a predetermined threshold value, with the mask.

The method may further include: scaling the input time series data in a predetermined size range; and quantizing the scaled time series data by dividing the scaled time series data into a plurality of size intervals and mapping time series data values, each matching a corresponding one of the size intervals, with a predetermined integer value.

The first masking may include: tokenizing the quantized time series data; and randomly covering a portion of the quantized time series data with the mask.

The generation of the first-restored time series data may include: generating an embedding vector by embedding the time series data, the portion of which is covered with the mask; generating a restored embedding vector by inputting the embedding vector to the generator; and performing reverse embedding to the restored embedding vector, thereby generating the first-restored time series data.

The generation of the embedding vector may include: performing first embedding to each quantized value of the time series data, the portion of which is covered with the mask; and performing second embedding to each time series order of the first-embedded time series data.

The generation of the first-restored time series data by performing the reverse embedding may include: calculating a similarity between the restored embedding vector and the first embedding vector produced by the first embedding; and converting the restored embedding vector to the first-restored time series data by selecting a maximum value of the similarity between the restored embedding vector and the first embedding vector at each position of the time series data as a quantized value at the corresponding position.

The generation of the first-restored time series data may include training the generator so that the difference between the first-restored time series data and the original time series data is minimized. The generation of the second-restored time series data may include training the generator so that the difference between the second-restored time series data and the original time series data is minimized.

The method may further include: calculating mean restored time series data by averaging the first-restored time series data and the second-restored time series data; and training the generator so that a difference between the mean restored time series data and the original time series data is minimized.

The method may further include inputting the original time series data and the first-restored time series data or the original time series data and the second-restored time series data to a discriminator and classifying the original time series data and the first-restored time series data or the original time series data and the second-restored time series data by the discriminator.

The discriminator may be trained to classify the original time series data as true and the first-restored time series data or the second-restored time series data as false. The generator may be trained to generate the first-restored time series data and the second-restored time series data so that a difference between the original time series data and the first-restored time series data classified by the discriminator or between the original time series data and the second-restored time series data classified by the discriminator is reduced.

According to an embodiment, provided is a computing device including: one or more processors; a memory; and one or more programs configured to be stored in the memory and executed by the one or more processors. The one or more programs may include: an instruction to perform first masking to cover a portion of input time series data with a mask; an instruction to generate first-restored time series data in which the time series data is restored by inputting the first-masked time series data to a generator; an instruction to calculate a difference between the first-restored time series data and original time series data; an instruction to perform second masking to cover a portion of the time series data with a mask on basis of the calculated difference; and an instruction to generate second-restored time series data in which the time series data is restored by inputting the second-masked time series data to the generator.

The first masking may randomly cover the portion of the input time series data, and the second masking covers the portion of the time series data, in which the difference between the first-restored time series data and the original time series data is equal to or greater than a predetermined threshold value, with the mask.

The one or more programs may further include: an instruction to scale the input time series data in a predetermined size range; and an instruction to quantize the scaled time series data by dividing the scaled time series data into a plurality of size intervals and mapping time series data values, each matching a corresponding one of the size intervals, with a predetermined integer value.

The instruction to perform the first masking may include: an instruction to tokenize the quantized time series data; and an instruction to randomly cover a portion of the quantized time series data with the mask.

The instruction to generate the first-restored time series data may include: an instruction to generate an embedding vector by embedding the time series data, the portion of which is covered with the mask; an instruction to generate a restored embedding vector by inputting the embedding vector to the generator; and an instruction to perform reverse embedding to the restored embedding vector, thereby generating the first-restored time series data.

The instruction to generate the embedding vector may include: an instruction to perform first embedding to each quantized value of the time series data, the portion of which is covered with the mask; and an instruction to perform second embedding to each time series order of the first-embedded time series data.

The instruction to generate the first-restored time series data by performing the reverse embedding may include: an instruction to calculate a similarity between the restored embedding vector and the first embedding vector produced by the first embedding; and an instruction to convert the restored embedding vector to the first-restored time series data by selecting a maximum value of the similarity between the restored embedding vector and the first embedding vector at each position of the time series data as a quantized value at the corresponding position.

The instruction to generate the first-restored time series data may include an instruction to train the generator so that the difference between the first-restored time series data and the original time series data is minimized. The instruction to generate the second-restored time series data may include an instruction to train the generator so that the difference between the second-restored time series data and the original time series data is minimized.

The one or more programs may include: an instruction to calculate mean restored time series data by averaging the first-restored time series data and the second-restored time series data; and an instruction to train the generator so that a difference between the mean restored time series data and the original time series data is minimized.

The one or more programs may further include an instruction to input the original time series data and the first-restored time series data or the original time series data and the second-restored time series data to a discriminator and classify the original time series data and the first-restored time series data or the original time series data and the second-restored time series data by the discriminator.

The discriminator may be trained to classify the original time series data as true and the first-restored time series data or the second-restored time series data as false. The generator may be trained to generate the first-restored time series data and the second-restored time series data so that a difference between the original time series data and the first-restored time series data classified by the discriminator or between the original time series data and the second-restored time series data classified by the discriminator is reduced.

According to embodiments of the present disclosure, an abnormality in time series data can be detected using a transformer-based artificial neural network. Thus, the abnormality in the time series data can be detected using a single artificial neural network without having to use a plurality of decoders. Due to the use of the deep learning model suitable for processing the time series data, normal distribution of the time series data can be properly learned, thereby improving abnormality detection performance.

BRIEF DESCRIPTION OF THE DRAWINGS

The above and other objectives, features, and advantages of the present disclosure will be more clearly understood from the following detailed description, taken in conjunction with the accompanying drawings, in which.

DETAILED DESCRIPTION

Hereinafter, specific embodiments will be described with reference to the accompanying drawings. The following detailed description is provided to assist in a comprehensive understanding of at least one of a method, a device, and a system to be described herein. However, the detailed description is merely exemplary, and the present disclosure is not limited thereto.

In the description of embodiments, a detailed description of known technologies related to the present disclosure will be omitted in the situation in which the subject matter of the present disclosure may be rendered rather unclear thereby. Terms to be used hereinafter will be defined in consideration of functions thereof in embodiments of the present disclosure, but may vary depending on the intentions of users or operators, as well as practices. Therefore, the terms shall be defined on the basis of the descriptions throughout the specification. The terms used in the detailed description shall be interpreted as being illustrative, while not being limitative, of embodiments. Unless clearly used otherwise, a singular form includes a plural meaning. It shall be understood that expressions such as "comprise," "include," and "have" used herein are for indicating certain features, numbers, steps, operations, elements, a part or combinations thereof and are not to be interpreted as excluding the presence or possibility of one or more features, numbers, steps, operations, elements, a part or combinations thereof other than the above.

In addition, terms, such as first and second, may be used to describing a variety of components, but the components are not Limited by such terms. Such terms may be used to distinguish one component from other components. For example, a first component may be referred to as a second component and, in a similar manner, a second component may be referred to as a first component without departing from the scope of the present disclosure.

Figure 1:
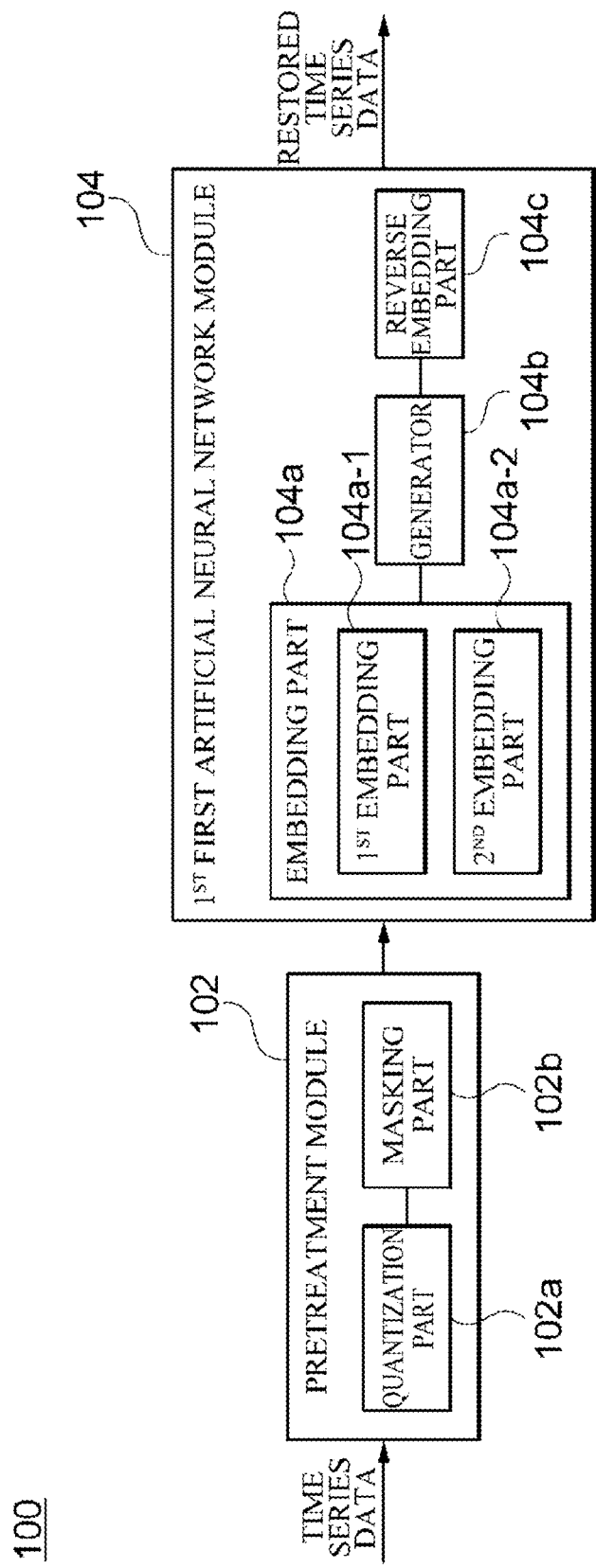
FIG. 1 illustrates a configuration of a device for detecting an abnormality in time series data according to an embodiment of the present disclosure.

FIG. 1 illustrates a configuration of a device for detecting an abnormality in time series data according to an embodiment of the present disclosure.

Referring to FIG. 1, an abnormality detection device 100 may include a pretreatment module 102 and a first artificial neural network module 104. The abnormality detection device 100 is a device for detecting an abnormality in time series data, and uses machine learning technology to detect an abnormality.

The pretreatment module 102 may perform pretreatment to input time series data. For example, the time series data may include heart rate data, brain wave data, temperature data, humidity data, precipitation data, quarterly sales performance data, traffic volumes, and the like, but is not limited thereto. The pretreatment module 102 may include a quantization part 102a and a masking part 102b.

The quantization part 102a may scale the input time series data in a predetermined size range. For example, the quantization part 102a may scale the input time series data with a value between −1 and 1. The quantization part 102a may quantize the time series data, scaled with a value between −1 and 1, according to the value thereof.

Figure 2:
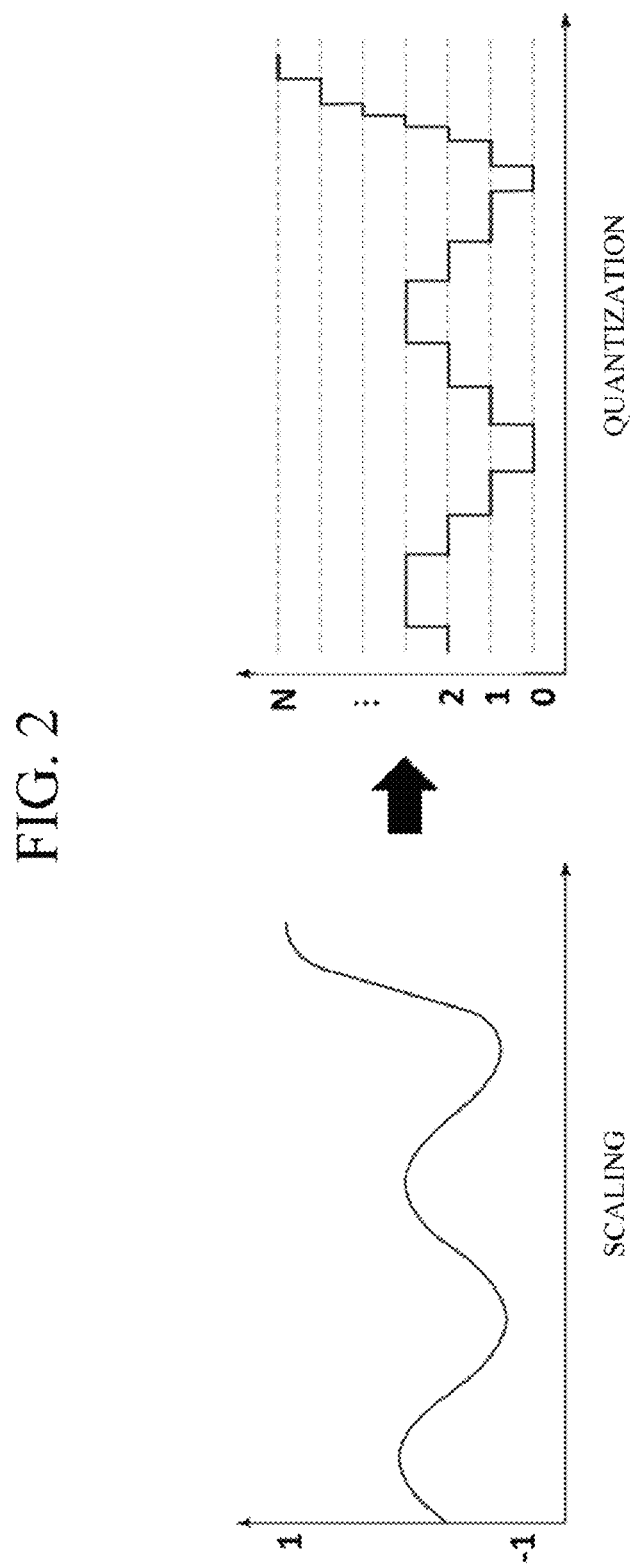
FIG. 2 illustrates a process of quantizing time series data according to an embodiment of the present disclosure.

FIG. 2 illustrates a process of quantizing time series data according to an embodiment of the present disclosure. Referring to FIG. 2, the quantization part 102a may divide the time series data between −1 and 1 into a plurality of size intervals. The quantization part 102a may quantize a time series data value matching each of the size intervals by mapping the time series data value with a predetermined integer value (e.g., 0, 1, 2, 3, . . . , or N). Here, the integer value may be equal to or greater than 0, but is not limited thereto.

The masking part 102b may generate tokens in predetermined units by tokenizing the quantized time series data. For example, the masking part 102b may generate tokens by tokening each value (i.e., a mapped integer value) of the quantized time series data.

The masking part 102b may cover a portion of the tokenized time series data with a mask. In an example embodiment, the masking part 102b may perform a masking operation of covering a predetermined ratio of the tokenized time series data with the mask. Here, the masking part 102b may randomly cover a predetermined ratio of the tokenized time series data with a mask or a specific portion of the tokenized time series data according to the training process of the first artificial neural network module 104.

The first artificial neural network module 104 may receive the pretreated time series data from the pretreatment module 102, and be trained to detect an abnormality in the input time series data. In an example embodiment, the first artificial neural network module 104 may include an artificial neural network based on a transformer. The transformer is an artificial neural network adopting self-attention while using an encoder-encoder architecture, i.e., a sequence-to-sequence architecture. The first artificial neural network module 104 may learn the context of an input sequence by calculating the concentration ratio of each of the tokens by multi-head self-attention.

The first artificial neural network module 104 may include an embedding part 104a, a generator 104b, and a reverse embedding part 104c. The embedding part 104a may generate embedded data by receiving the tokenized time series data, a portion of which is covered with a mask, from the masking part 102b, and embedding the input time series data. The embedding part 104a may include a first embedding part 104a-1 and a second embedding part 104a-2.

Figure 3:
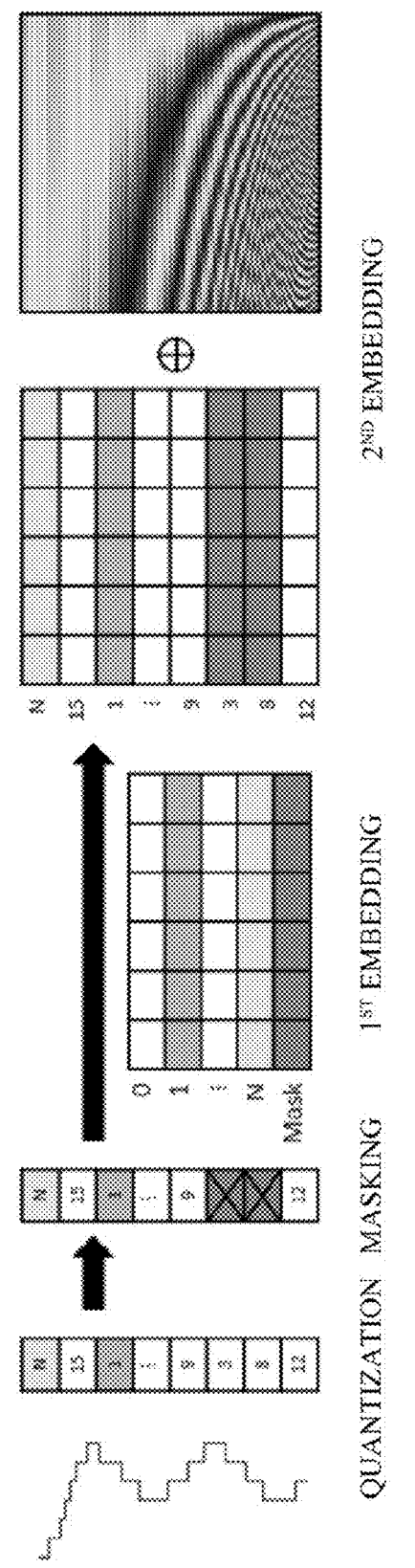
FIG. 3 schematically illustrates a process of embedding time series data according to an embodiment of the present disclosure.

FIG. 3 schematically illustrates a process of embedding time series data according to an embodiment of the present disclosure. Referring to FIG. 3, the first embedding part 104a-1 may perform first embedding to the tokenized time series data, a portion of which is covered with a mask. In this case, the first embedding part 104a-1 may form a first embedding vector by performing the first embedding to each quantized value (i.e., an integer indicating the size of the time series data) of the time series data. Here, the first embedding vector may have a matrix form matching a vector dimension corresponding to the total number of integers for quantization (i.e., the total number of size intervals in FIG. 2)×one quantized value.

The second embedding part 104a-2 may perform second embedding to the first-embedded time series data. The second embedding part 104a-2 may generate an embedding vector by performing the second embedding to the time series order of the first-embedded time series data. Consequently, time-series position information may be imparted to the corresponding embedding vector.

The generator 104b may be an artificial neural network trained to restore the original time series data using the embedding vector, generated by the embedding part 104a, as an input. That is, the embedding vector is configured such that a portion of the time series data is covered with a mask. Here, the generator 104b may learn to restore the portion of the embedding vector covered with a mask.

Figure 4:
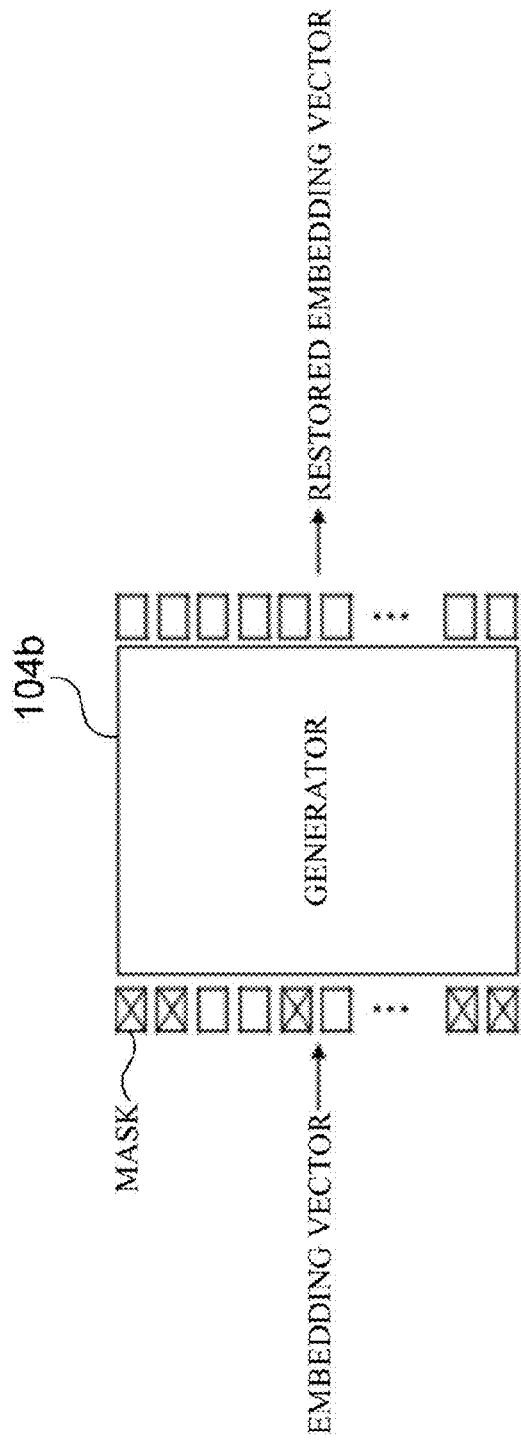
FIG. 4 schematically illustrates a situation in which the generator restores a portion of time series data covered with a mask, according to an embodiment of the present disclosure.

FIG. 4 schematically illustrates a situation in which the generator 104b restores a portion of time series data covered with a mask, according to an embodiment of the present disclosure. When the embedding vector is input, the generator 104b may output a restored embedding vector on the basis of the embedding vector.

The reverse embedding part 104c may perform reverse embedding to the restored embedding vector output from the generator 104b. The reverse embedding part 104c may convert the restored embedding vector into an input data form, i.e., the form of the time series data input to the artificial neural network module 104 by the reverse embedding. Here, the input data form may be a data form obtained by quantizing the time series data.

Figure 5:
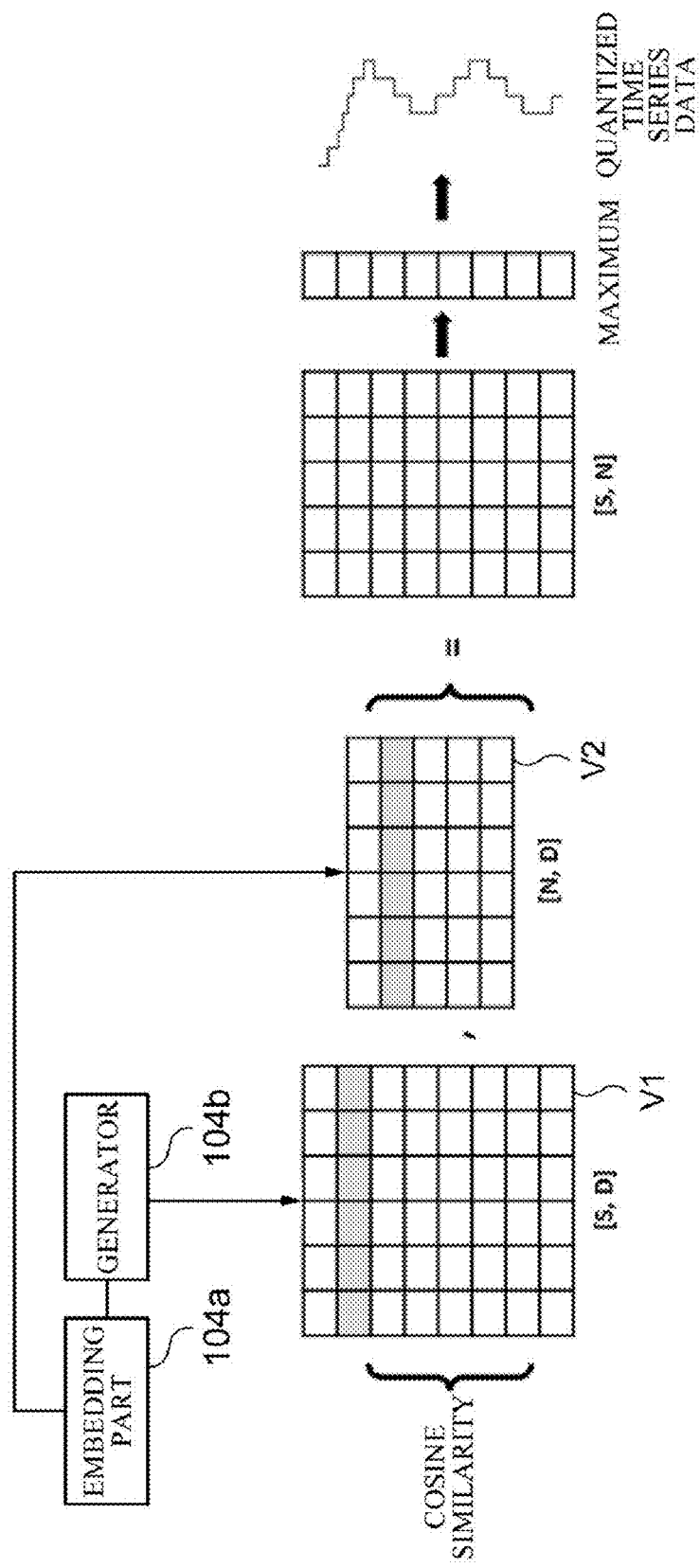
FIG. 5 illustrates a process of covering a restored embedding vector into an input data form according to an embodiment of the present disclosure.

FIG. 5 illustrates a process of covering a restored embedding vector into an input data form according to an embodiment of the present disclosure. Referring to FIG. 5, the reverse embedding part 104c may calculate the similarity between a restored embedding vector V1 output from the generator 104b and a first embedding vector V2 produced by the embedding of the embedding part 104a.

Here, the restored embedding vector V1 may have the shape of a matrix matching a vector dimension D corresponding to a product of the length S of the time series data×one quantized value. In addition, the first embedding vector V2 may have the shape of a matrix matching a vector dimension D corresponding a product of the total number N of integers for quantization×one quantized value.

The reverse embedding part 104c may convert the restored embedding vector into the input data form by selecting the maximum value of the similarity between the restored embedding vector V1 and the first embedding vector V2 at each position of the time series data as a quantized value.

The first artificial neural network module 104 may compare restored time series data output from the reverse embedding part 104c with an answer value (i.e., original time series data) so that the parameters of the generator 104b are learned.

Figure 6:
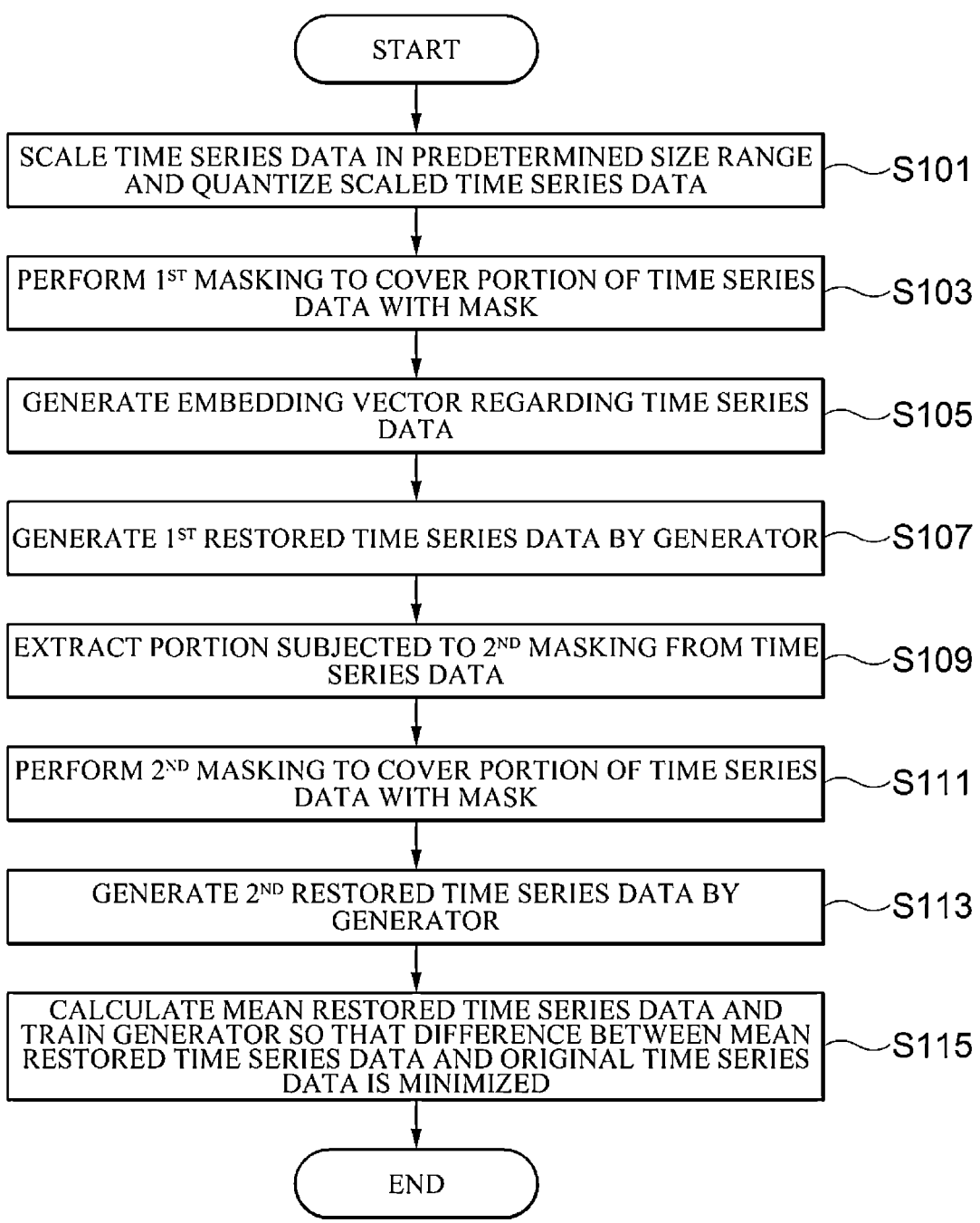
FIG. 6 is a flowchart illustrating a method of detecting an abnormality in time series data according to an embodiment of the present disclosure.

FIG. 6 is a flowchart illustrating a method of detecting an abnormality in time series data according to an embodiment of the present disclosure. Although the method is illustrated as including a plurality of operations in the flowchart illustrated in FIG. 6, at least some of operations may be performed in different orders, be combined and performed with other operations, or be divided into sub-operations, or one or more operations (not shown) may be added.

Referring to FIG. 6, in S101, the pretreatment module 102 scales input time series data in a predetermined size range and then quantizes the scaled time series data. That is, the pretreatment module 102 may scale the time series data in the predetermined size range, and then quantize the scaled time series data by dividing the scaled time series data into a plurality of size intervals and mapping time series data values matching the size intervals with predetermined integer values.

Afterwards, in S103, the pretreatment module 102 perform first masking to cover a portion of the quantized time series data with a mask. Here, the pretreatment module 102 may randomly cover a predetermined ratio of the quantized time series data.

Subsequently, in S105, the first artificial neural network module 104 generates an embedding vector by receiving the time series data, the portion of which is randomly covered with a mask, from the pretreatment module 102 and embedding the input time series data.

Specifically, the first artificial neural network module 104 may generate the embedding vector by performing first embedding to each quantized value of the time series data randomly covered with a mask and then second embedding to each time series order of the first-embedded time series data.

Afterwards, in S107, the first artificial neural network module 104 outputs first-restored time series data in which the portion randomly covered with the mask is restored by inputting the embedding vector to the generator 104b.

Here, the first artificial neural network module 104 outputting the first-restored time series data may include converting the restored embedding vector, output from the generator 104b, into an input data form.

Subsequently, in S109, the first artificial neural network module 104 extracts a portion to be second-masked from the time series data by comparing the first-restored time series data and the original time series data (i.e., the time series data, a portion of which is not covered with a mask, as an answer value).

Specifically, the first artificial neural network module 104 may calculate the difference between the first-restored time series data and the original time series data at each time series position. The first artificial neural network module 104 may line up differences between the first-restored time series data and the original time series data in the descending order and extract any difference equal to or greater than a predetermined threshold value as a portion to be second-masked. Here, the first artificial neural network module 104 may be first trained so that the difference between the first-restored time series data and the original time series data is minimized.

Afterwards, in S111, the pretreatment module 102 performs second masking to cover a portion of the quantized time series data, in which the difference between the first-restored time series data and the original time series data is equal to or greater than the predetermined threshold value, with a mask Subsequently, in S113, the first artificial neural network module 104 receives the second-masked time series data from the pretreatment module 102 and outputs second-restored time series data, in which the second-masked portion is restored.

Here, the first artificial neural network module 104 outputting the second-restored time series data may include generating the embedding vector by embedding the second-masked time series data, outputting the restored embedding vector by inputting the generated embedding vector to the generator 104b, and converting the output restored embedding vector into an input data form.

Here, the first artificial neural network module 104 may be second trained to compare the second-restored time series data and the original time series data so that the difference between the second-restored time series data and the original time series data is minimized.

Afterwards, in mean restored data, the first artificial neural network module 104 calculates mean restored time series data by averaging the first-restored time series data and the second-restored time series data and trains the generator 104b so that the difference between the mean restored time series data and the original time series data is minimized. That is, the first artificial neural network module 104 may be third trained so that the difference between the mean restored time series data and the original time series data is minimized.

Here, in the training process of the first artificial neural network module 104, normal data may only be used as the time series data. That is, the first artificial neural network module 104 may perform machine learning only using normal time series data. When the training of the first artificial neural network module 104 is finished, the time series data may be input to the first artificial neural network module 104 in an inference process in order to determine whether or not the time series data has an abnormality.

According to the disclosed embodiment, an abnormality in time series data can be detected using a transformer-based artificial neural network. Thus, the abnormality in the time series data can be detected using a single artificial neural network without having to use a plurality of decoders. Due to the use of the deep learning model suitable for processing the time series data, normal distribution of the time series data can be properly learned, thereby improving abnormality detection performance.

The term "module" used herein may refer to a functional and structural combination of hardware for realizing the technical principle of the present disclosure and software for driving the hardware. For example, the module may mean a logical unit of specific codes and a hardware resource by which the specific codes are to be performed. The module does not necessarily mean physically connected codes or a single type of hardware.

Figure 7:
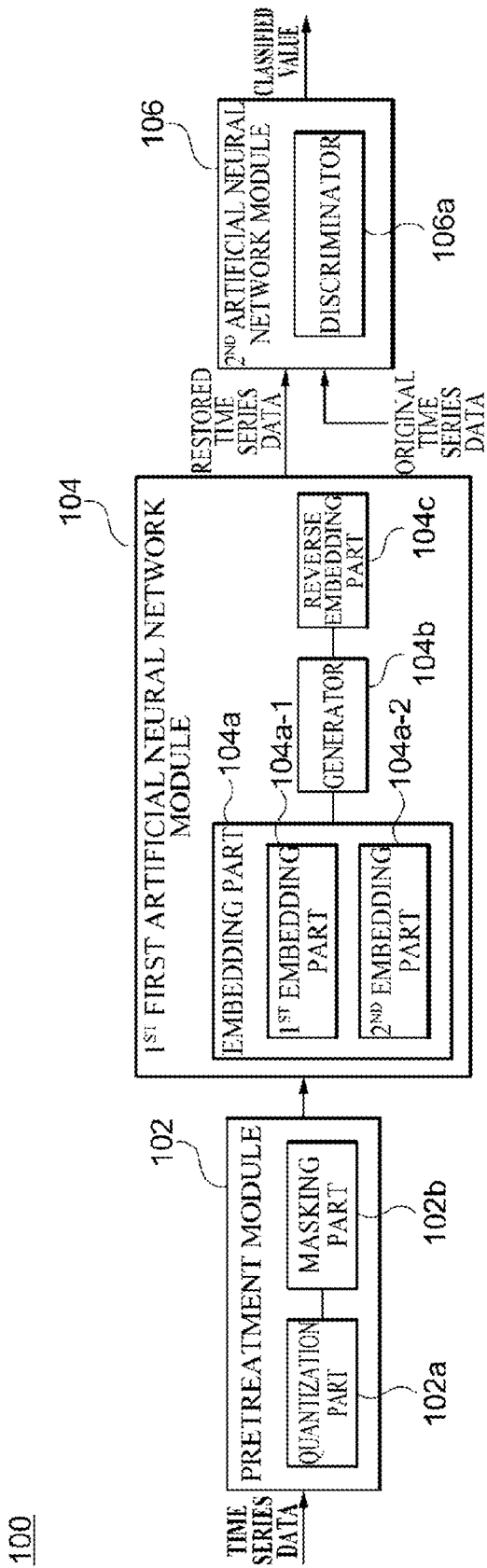
FIG. 7 illustrates a configuration of a device for detecting an abnormality in time series data according to another embodiment of the present disclosure.

FIG. 7 illustrates a configuration of a device for detecting an abnormality in time series data according to another embodiment of the present disclosure. Here, features different from those of the embodiment illustrated in FIG. 1 will mainly be described.

Referring to FIG. 7, the abnormality detection device 100 may include a pretreatment module 102, a first artificial neural network module 104, and a second artificial neural network module 106. Here, the pretreatment module 102 and the first artificial neural network module 104 are the same as or similar to those of the former embodiment illustrated in FIG. 1, and thus detailed descriptions thereof will be omitted.

In the illustrated embodiment, the second artificial neural network module 106 may include a transformer-based artificial neural network. The second artificial neural network module 106 and the first artificial neural network module 104 may constitute a generative adversarial model. In this generative adversarial model, the first artificial neural network module 104 may serve as a generator, whereas the second artificial neural network module 106 may serve as a discriminator.

The second artificial neural network module 106 may receive the original time series data and the restored time series data output from the first artificial neural network module 104. Here, a CLS token may be inserted into the head portion of each of the original time series data and the restored time series data input to the second artificial neural network module 106. Here, the CSL token may indicate a vector token used in classification.

The second artificial neural network module 106 may include a discriminator 106a. The discriminator 106a may be an artificial neural network trained to classify the original time series data as true and the restored time series data as false. Here, the first artificial neural network module 104 may be trained to generate the restored time series data so that the difference between the original time series data and the restored time series data classified by the discriminator 106a. In this manner, the first artificial neural network module 104 may generate the restored time series data to be more similar to the original time series data. The first artificial neural network module 104 and the second artificial neural network module 106 may be trained in an alternating manner.

In addition, in the training process of the first artificial neural network module 104, the second artificial neural network module 106 may also be trained. For example, the CLS token may be inserted into the head portion of each of the first-restored time series data, the second-restored time series data, the mean restored time series data, and the like, input to the second artificial neural network module 106, and then classified by the second artificial neural network module 106.

Figure 8:
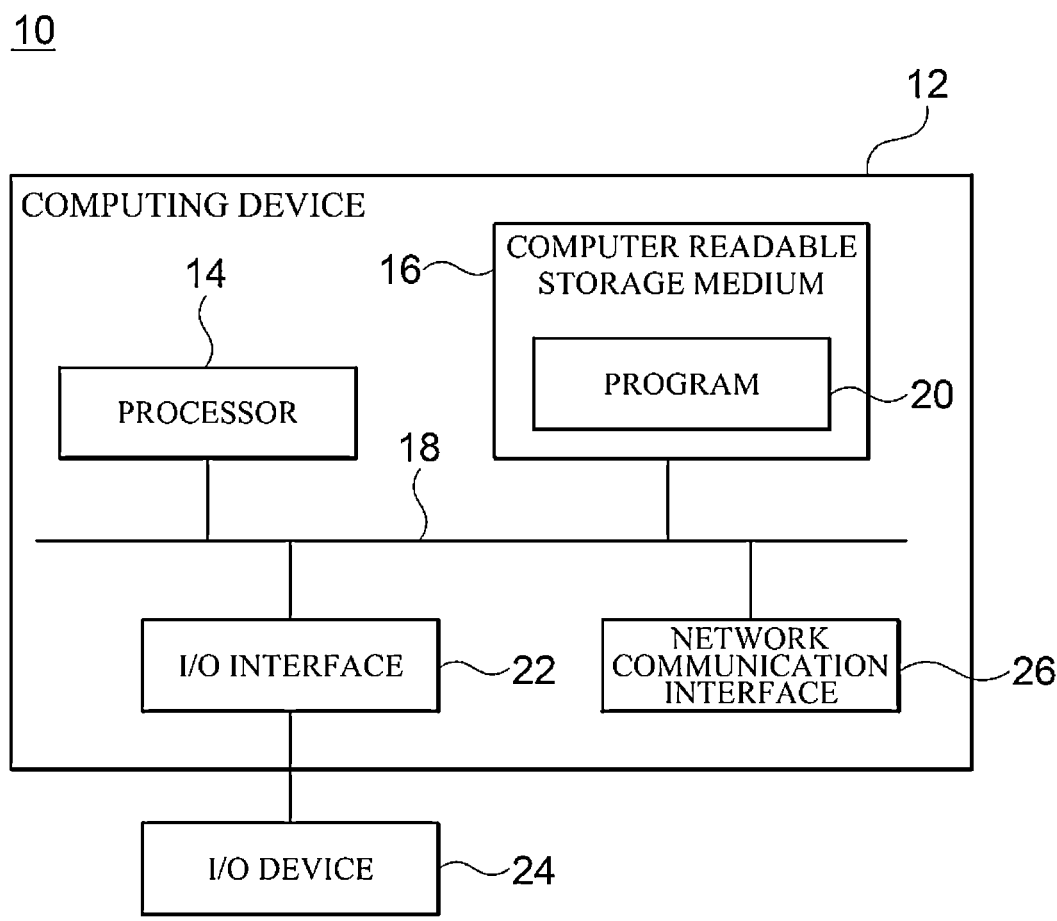
FIG. 8 is a block diagram illustrating a computing environment including a computing apparatus suitable to be used in example embodiments.

FIG. 8 is a block diagram illustrating a computing environment 10 including a computing apparatus suitable to be used in example embodiments. In the illustrated embodiments, each component may have a function and capability different from those to be described below, and additional components not described below may be included.

The illustrated computing environment 10 includes a computing device 12. According to an embodiment, the computing device 12 may be the locking apparatus 110. In addition, the computing device 12 may be the device 100 for detecting an abnormality in time series data.

The computing device 12 includes at least one processor 14, a computer readable storage medium 16, and a communication bus 18. The processor 14 may allow the computing device 12 to operate according to the example embodiments described above. For example, the processor 14 may execute one or more programs stored in the computer readable storage medium 16. The one or more programs may include one or more computer executable instructions. The computer executable instructions may be configured to allow the computing device 12 to perform the operations according to the example embodiments when executed by the processor 14.

The computer readable storage medium 16 may be configured to store computer executable instructions, program codes, program data, and/or other suitable forms of information. A program 20 stored in the computer readable storage medium 16 may include a set of instructions executable by the processor 14. According to an embodiment, the computer readable storage medium 16 may be a memory (e.g., a volatile memory such as a random access memory (RAM), a non-volatile memory, or a combination thereof), one or more magnetic disk storage devices, optical disk storage devices, flash memory devices, other types of storage media which can be accessed by the computing device 12 and store intended information, or combinations thereof.

The communication bus 18 may interconnect various components of the computing device 12, including the processor 14 and the computer readable storage medium 16, to each other.

The computing device 12 may further include one or more input/output (I/O) interfaces 22 providing an interface for one or more I/O devices 24 and one or more network communication interfaces 26. The I/O interface 22 and the network communication interfaces 26 may be connected to the communication bus 18. The I/O devices 24 may be connected to other components of the computing device 12 through the I/O interfaces 22. The I/O devices 24 may include input devices, such as a pointing device (e.g., a mouse and a track pad), a keyboard, a touch input device (e.g., a touch pad and a touch screen), a voice or sound input device, various types of sensors, and/or a capturing device, and/or output devices, such as a display device, a printer, a speaker, and/or a network card. Each of the I/O devices 24 may be one component constituting the computing device 12, may be included in the computing device 12, or may be connected to the computing device 12 as a device separate from the computing device 12.

Although the exemplary embodiments of the present disclosure have been described in detail hereinabove, a person having ordinary knowledge in the technical field to which the present disclosure pertains will appreciate that various modifications are possible to the foregoing embodiments without departing from the scope of the present disclosure. Therefore, the scope of protection of the present disclosure shall not be limited to the foregoing embodiments but shall be defined by the appended Claims and equivalents thereof.

What is claimed is:

1. A method of detecting an abnormality in time series data, the method being performed in a computing device including one or more processors and a memory storing one or more programs executed by the one or more processors, the method comprising:
    first masking to cover a portion of input time series data with a mask;
    generating first-restored time series data in which the time series data is restored by inputting the first-masked time series data to a generator;
    calculating a difference between the first-restored time series data and original time series data;
    second masking to cover a portion of the time series data with a mask on basis of the calculated difference; and
    generating second-restored time series data in which the time series data is restored by inputting the second-masked time series data to the generator.

2. The method of claim 1, wherein the first masking randomly covers the portion of the input time series data, and
    the second masking covers the portion of the time series data, in which the difference between the first-restored time series data and the original time series data is equal to or greater than a predetermined threshold value, with the mask.

3. The method of claim 1, further comprising:
    scaling the input time series data in a predetermined size range; and
    quantizing the scaled time series data by dividing the scaled time series data into a plurality of size intervals and mapping time series data values, each matching a corresponding one of the size intervals, with a predetermined integer value.

4. The method of claim 3, wherein the first masking comprises:
    tokenizing the quantized time series data; and
    randomly covering a portion of the quantized time series data with the mask.

5. The method of claim 4, wherein the generation of the first-restored time series data comprises:
    generating an embedding vector by embedding the time series data, the portion of which is covered with the mask;
    generating a restored embedding vector by inputting the embedding vector to the generator; and
    performing reverse embedding to the restored embedding vector, thereby generating the first-restored time series data.

6. The method of claim 5, wherein the generation of the embedding vector comprises:
    performing first embedding to each quantized value of the time series data, the portion of which is covered with the mask; and
    performing second embedding to each time series order of the first-embedded time series data.

7. The method of claim 6, wherein the generation of the first-restored time series data by performing the reverse embedding comprises:
    calculating a similarity between the restored embedding vector and the first embedding vector produced by the first embedding; and
    converting the restored embedding vector to the first-restored time series data by selecting a maximum value of the similarity between the restored embedding vector and the first embedding vector at each position of the time series data as a quantized value at the corresponding position.

8. The method of claim 1, wherein the generation of the first-restored time series data comprises training the generator so that the difference between the first-restored time series data and the original time series data is minimized, and
    the generation of the second-restored time series data comprises training the generator so that the difference between the second-restored time series data and the original time series data is minimized.

9. The method of claim 8, further comprising:
    calculating mean restored time series data by averaging the first-restored time series data and the second-restored time series data; and
    training the generator so that a difference between the mean restored time series data and the original time series data is minimized.

10. The method of claim 8, further comprising inputting the original time series data and the first-restored time series data or the original time series data and the second-restored time series data to a discriminator and classifying the original time series data and the first-restored time series data or the original time series data and the second-restored time series data by the discriminator.

11. The method of claim 10, wherein the discriminator is trained to classify the original time series data as true and the first-restored time series data or the second-restored time series data as false, and
    the generator is trained to generate the first-restored time series data and the second-restored time series data so that a difference between the original time series data and the first-restored time series data classified by the discriminator or between the original time series data and the second-restored time series data classified by the discriminator is reduced.

12. A computing device comprising:
    one or more processors;
    a memory; and
    one or more programs,
    wherein the one or more programs are configured to be stored in the memory and executed by the one or more processors, and
    the one or more programs comprise:
    an instruction to perform first masking to cover a portion of input time series data with a mask;
    an instruction to generate first-restored time series data in which the time series data is restored by inputting the first-masked time series data to a generator;
    an instruction to calculate a difference between the first-restored time series data and original time series data;
    an instruction to perform second masking to cover a portion of the time series data with a mask on basis of the calculated difference; and
    an instruction to generate second-restored time series data in which the time series data is restored by inputting the second-masked time series data to the generator.

13. The computing device of claim 12, wherein the first masking randomly covers the portion of the input time series data, and the second masking covers the portion of the time series data, in which the difference between the first-restored time series data and the original time series data is equal to or greater than a predetermined threshold value, with the mask.

14. The computing device of claim 12, wherein the one or more programs further comprise:
an instruction to scale the input time series data in a predetermined size range; and
an instruction to quantize the scaled time series data by dividing the scaled time series data into a plurality of size intervals and mapping time series data values, each matching a corresponding one of the size intervals, with a predetermined integer value.

15. The computing device of claim 14, wherein the instruction to perform the first masking comprises:
an instruction to tokenize the quantized time series data; and
an instruction to randomly cover a portion of the quantized time series data with the mask.

16. The computing device of claim 15, wherein the instruction to generate the first-restored time series data comprises:
an instruction to generate an embedding vector by embedding the time series data, the portion of which is covered with the mask;
an instruction to generate a restored embedding vector by inputting the embedding vector to the generator; and
an instruction to perform reverse embedding to the restored embedding vector, thereby generating the first-restored time series data.

17. The computing device of claim 16, wherein the instruction to generate the embedding vector comprises:
an instruction to perform first embedding to each quantized value of the time series data, the portion of which is covered with the mask; and
an instruction to perform second embedding to each time series order of the first-embedded time series data.

18. The computing device of claim 17, wherein the instruction to generate the first-restored time series data by performing the reverse embedding comprises:
an instruction to calculate a similarity between the restored embedding vector and the first embedding vector produced by the first embedding; and
an instruction to convert the restored embedding vector to the first-restored time series data by selecting a maximum value of the similarity between the restored embedding vector and the first embedding vector at each position of the time series data as a quantized value at the corresponding position.

19. The computing device of claim 12, wherein the instruction to generate the first-restored time series data comprises an instruction to train the generator so that the difference between the first-restored time series data and the original time series data is minimized, and
the instruction to generate the second-restored time series data comprises an instruction to train the generator so that the difference between the second-restored time series data and the original time series data is minimized.

20. The computing device of claim 19, wherein the one or more programs comprise:
an instruction to calculate mean restored time series data by averaging the first-restored time series data and the second-restored time series data; and
an instruction to train the generator so that a difference between the mean restored time series data and the original time series data is minimized.

21. The computing device of claim 19, wherein the one or more programs further comprise an instruction to input the original time series data and the first-restored time series data or the original time series data and the second-restored time series data to a discriminator and classify the original time series data and the first-restored time series data or the original time series data and the second-restored time series data by the discriminator.

22. The computing device of claim 21, wherein the discriminator is trained to classify the original time series data as true and the first-restored time series data or the second-restored time series data as false, and
the generator is trained to generate the first-restored time series data and the second-restored time series data so that a difference between the original time series data and the first-restored time series data classified by the discriminator or between the original time series data and the second-restored time series data classified by the discriminator is reduced.

23. A computer program stored in a non-transitory computer readable storage medium and comprising one or more instructions, wherein, when executed by a computing device including one or more processors, the one or more instructions enable the computing device to perform:
first masking to cover a portion of the input time series data with a mask;
generating first-restored time series data in which the time series data is restored by inputting the first-masked time series data to a generator;
calculating a difference between the first-restored time series data and original time series data;
second masking to cover the time series data with a mask on basis of the calculated difference; and
generating second-restored time series data in which the time series data is restored by inputting the second-masked time series data to the generator.

* * * * *